United States Patent [19]

Jamieson et al.

[11] 4,241,073

[45] Dec. 23, 1980

[54] TREATMENT OF IMMEDIATE HYPERSENSITIVITY DISEASES WITH ARYL HYDANTOINS

[75] Inventors: William B. Jamieson, Woking; William J. Ross, Lightwater; Robin G. Simmonds, Wokingham; John P. Verge, Henley-on-Thames, all of England

[73] Assignee: Lilly Industries Limited, London, England

[21] Appl. No.: 39,075

[22] Filed: May 14, 1979

[30] Foreign Application Priority Data

May 23, 1978 [GB] United Kingdom ............... 21352/78

[51] Int. Cl.$^3$ .......................................... A61K 31/415
[52] U.S. Cl. ............................... 424/273 R; 542/442; 548/308; 548/309; 548/314
[58] Field of Search ................ 542/442; 548/308, 309, 548/314; 424/273 R

[56] References Cited

U.S. PATENT DOCUMENTS

| 2,479,065 | 8/1949 | Gresham | 548/308 |
|---|---|---|---|
| 3,365,296 | 1/1968 | Cox et al. | 542/442 |
| 3,395,153 | 7/1968 | Kitasaki et al. | 548/308 |
| 3,847,933 | 11/1974 | Tyler | 548/308 |

FOREIGN PATENT DOCUMENTS

846601  8/1960  United Kingdom ..................... 548/308

OTHER PUBLICATIONS

Aspelund et al. Chem. Abst. 1968, vol. 68, No. 49512m.
Derkosch Chem. Abst. 1962, vol. 56, col. 3038-3039.
Finkbeiner I J. Amer. Chem. Soc. 1964, vol. 86, pp. 961-962.
Finkbeiner II Chem. Abst. 1965, vol. 62, col. 16258-16259.
Hahn et al. I J. Amer. Chem. Soc. 1925, vol. 47, pp. 2953-2961.
Hahn et al. II J. Amer. Chem. Soc. 1925, vol. 47, pp. 147-163.
Attia et al. Chem. Abst. 1977, vol. 86, No. 188,987e.
Johnson et al. J. Amer. Chem. Soc. 1912, vol. 34, pp. 1048-1054.
Musial Chem. Abst. 1962. vol. 57, col. 11188-11189.
Musial et al. I Chem. Abst. 1963, vol. 59, col. 8726-8727.
Musial et al. II Chem. Abst. 1963, vol. 59, col. 10020.
Musial et al. III Chem. Abst. 1967, vol. 67, No. 116851r.
Mustafa et al. Chem. Abst. 1971, vol. 75, No. 88522d.
Rutkovskii et al. Chem. Abst. 1971, vol. 74, No. 69783c.
Shirai et al. I & II Chem. Abst. 1960, vol. 54, col. 3388-3389.
Shirai et al. III Chem. Abst. 1967, vol. 67, No. 32646q.
Shirai et al. IV Chem. Abst. 1968, vol. 68, No. 87239k.
Stuckey Chem. Abst. 1949, vol. 43, col. 6984.
Lombardino et al. J. Med. Chem. 1964, vol. 7, pp. 97-101.

*Primary Examiner*—Henry R. Jiles
*Assistant Examiner*—Richard A. Schwartz
*Attorney, Agent, or Firm*—James L. Rowe; Arthur R. Whale

[57] ABSTRACT

Novel hydantoin compounds are described of the formula (I):

$$\underset{\underset{R^2}{|}}{\overset{Ar}{\underset{|}{CHR^1}}}\underset{5\quad 1}{\diagdown}\underset{4\quad 3\quad 2}{N}\diagup\overset{R^3}{\underset{|}{N}}\diagdown O \qquad (I)$$

$$O=\overset{}{\underset{\underset{R^4}{|}}{N}}=O$$

wherein Ar is phenyl optionally substituted by up to three radicals selected from the group comprising $C_{1-6}$ alkoxy, halogen, 1,3-dioxol-2-yl, hydroxy $C_{1-4}$ alkoxy $C_{1-4}$ alkyl, phenyl, hydroxyl, nitrile, $C_{1-4}$ haloalkyl, $C_{1-4}$ alkyl, $C_{2-4}$ alkenyloxy, $C_{1-4}$ alkoxycarbonyl or phenoxy optionally substituted by $C_{1-4}$ haloalkyl, $C_{1-4}$ alkoxy or halogen;

or is thiophene optionally substituted by phenyl or by one or two $C_{1-4}$ alkyl groups;

$R^1$ and $R^2$ are independently hydrogen or taken together represent a chemical bond;

$R^3$ is hydrogen, $C_{1-6}$ alkyl or $C_{2-4}$ alkenyl; and $R^4$ is $C_{1-6}$ alkyl, $C_{2-4}$ alkenyl, phenyl or benzyl;

provided that $R^3$ cannot be hydrogen when Ar is unsubstituted phenyl and $R^4$ is n-butyl. The compounds are useful in the treatment of immediate hypersensitivity diseases including asthma.

3 Claims, No Drawings

TREATMENT OF IMMEDIATE HYPERSENSITIVITY DISEASES WITH ARYL HYDANTOINS

This invention relates to a class of new heterocyclic derivatives which have been found to possess useful pharmacological activity, to methods of making such compounds, to pharmaceutical formulations containing pharmacologically active compounds and to methods of preventing immediate hypersensitivity conditions by administration of said derivatives or formulations.

Lombardino and Gerber in the *Journal of Medicinal Chemistry* 7, 97–111 (1964) described certain 3,5-disubstituted hydantoin derivatives which they were investigating as potential hypoglycemic agents. They found that those compounds did not possess that pharmacological activity.

An object of the present invention is to provide substituted hydantoin derivatives which are effective in the prophylactic chemotherapy of immediate hypersensitivity conditions such as asthma.

Accordingly in a first aspect of the invention there is provided a hydantoin derivative of formula (I):

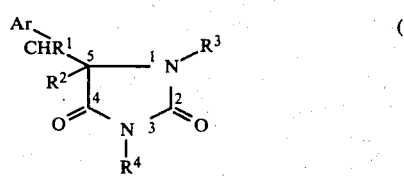

wherein
Ar is phenyl optionally substituted by up to three radicals selected from the group comprising $C_{1-6}$ alkoxy, halogen, 1,3-dioxol-2-yl, hydroxy $C_{1-4}$ alkoxy $C_{1-4}$ alkyl, phenyl, hydroxyl, nitrile, $C_{1-4}$ haloalkyl, $C_{1-4}$ alkyl, $C_{2-4}$ alkenyloxy, $C_{1-4}$ alkoxycarbonyl or phenoxy optionally substituted by $C_{1-4}$ haloalkyl, $C_{1-4}$ alkoxy or halogen;
or is thiophene optionally substituted by phenyl or by one or two $C_{1-4}$ alkyl groups;
$R^1$ and $R^2$ are independently hydrogen or taken together represent a chemical bond;
$R^3$ is hydrogen, $C_{1-6}$ alkyl or $C_{2-4}$ alkenyl; and
$R^4$ is $C_{1-6}$ alkyl, $C_{2-4}$ alkenyl, phenyl or benzyl;
provided that $R^3$ cannot be hydrogen when Ar is unsubstituted phenyl and $R^4$ is n-butyl.

According to a second aspect of the invention there is provided a pharmaceutical formulation which comprises a compound of formula (I) as defined above, or a compound of formula (I) in which $R^3$ is hydrogen when Ar is unsubstituted phenyl and $R^4$ is n-butyl; associated with a pharmaceutically-acceptable carrier therefor.

The compounds of formula (I) in which $R^1$ and $R^2$ both represent hydrogen, i.e. compounds of formula (II):

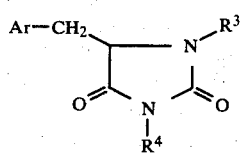

are preferred and can be prepared by reduction of the corresponding alkylidene compounds of formula (III):

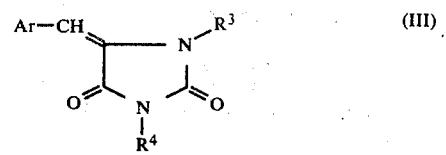

i.e. compounds of formula (I) in which $R^1$ and $R^2$ taken together represent a chemical bond.

This reduction method is provided as a further aspect of the invention and can be accomplished using hydrogen and conventional catalysts such as platinium or palladium absorbed onto charcoal. Any suitable inert organic solvent such as a liquid alkanol, e.g. ethanol, ethyl acetate or acetic acid can be employed. The reaction temperature is not critical although it is preferred to effect the reaction at temperatures within the range from 10° to 100° C.

Alternatively, the benzyl hydantoins of formula (II) may be prepared by reacting a compound of formula (IV):

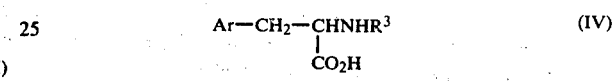

with an isocyanate of formula $R^4NCO$.

The reaction can be effected in the presence of an aqueous base such as caustic soda to form a compound of formula:

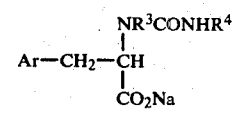

This salt can then be cyclised by acidification with a strong mineral acid such as hydrochloric acid using reaction conditions similar to those described in the *Journal of Heterocyclic Chemistry*, 10, 173 (1973). For example the reaction can be carried out at a temperature of from 20° C. to 100° C.

As can be seen from the above, the compounds of formula (III) are useful intermediates in the preparation of compounds of formula (II). However, it should be noted that these intermediates have useful pharmacological activity in their own right. They may be prepared by the reaction of a hydantoin derivative of formula (V):

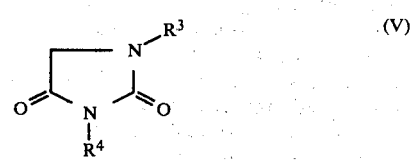

with an aldehyde of formula ArCHO. The reaction conditions necessary to effect this condensation will be well-known to those skilled in the art and are described in for example U.S. Pat. No. 2,861,079. For example, the reaction can be carried out in an organic solvent, such as for instance ethanol, at a temperature of from 20° C. to 100° C.

Preferred compounds of formula (I) are those in which $R^3$ is hydrogen and $R^4$ is n-butyl and Ar is unsubstituted phenyl, p-chlorophenyl, 3,4-dimethoxyphenyl, 2,4,5-triethoxyphenyl or p-t-butylphenyl.

When Ar is thiophene, it is preferably a thiophen-2-yl-group.

Thus the invention also provides a process for preparing a hydantoin of formula (I) which comprises:

(a) reacting a compound of the formula

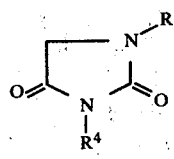

with an aldehyde of formula ArCHO, to give a compound of formula (I) wherein $R^1$ and $R^2$ represent a chemical bond;

(b) reducing a compound of formula (I) wherein $R^1$ and $R^2$ represent a chemical bond to give a compound of formula (I) wherein $R^1$ and $R^2$ are hydrogen; or (c) reacting a compound of the formula

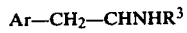

with an isocyanate of formula $R^4NCO$ to give a compound of formula (I) wherein $R^1$ and $R^2$ are hydrogen.

The compounds of formula (I) have been shown to be useful in the prophylactic treatment of asthma in mammals. This activity has been demonstrated in guinea pigs using either the "Herxheimer" test described in *Journal of Physiology (London)* 117, 251 (1952) or the "guinea pig chopped lung test" described by Mongar and Schild in *Journal of Physiology (London)* 131, 207 (1956) or Brocklehurst *Journal of Physiology (London)* 151, 416 (1960). The compounds have low toxicity.

The "Herxheimer" test is based on an allergic bronchospasm induced in guinea pigs which closely resembles an asthmatic attack in man. The mediators causing the bronchospasm are very similar to those released when sensitised human lung tissue is challenged with an antigen. Although the antibody involved is $I_gG_l$ in the guinea pig and $I_gE$ in man, both antibodies are homocytotrophic and bind strongly to tissue. Compounds of the invention have exhibited activity in the "Herxheimer" test at dosages ranging from 25 mg/kg to 200 mg/kg.

The compounds of formula (I) may be administered by various routes and for this purpose may be formulated in a variety of forms, although oral administration is preferred. Thus the compounds of the invention may be administered by the oral and rectal routes, topically, parenterally, e.g. by injection, in the form of, for example, tablets, lozenges, sublingual tablets, sachets, cachets, elixirs, suspensions, aerosols, ointments, for example containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula I. Dosages of from 0.5 to 300 mg/kg per day, preferably 1 to 20 mg/kg of active ingredient may be administered although it will, of course, readily be understood that the amount of the compound of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidine, cetostearyl alcohol, starch, modified starches, gum acacia, calcium phosphate, cocoa butter, ethoxylated esters, oil of thoobroma, arachis oil, alginates, tragacanth, gelatin, syrup B.P., methyl cellulose,polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The following non-limitative examples further illustrate the invention.

EXAMPLE 1

3-n-Butyl-5-(2,4,5-trimethoxybenzylidene) hydantoin

A mixture of 2,4,5-trimethoxybenzaldehyde (9.8 g; 0.05 mole), 3-n-butylhydantoin (7.8 g: 0.05 mole) and ethanolamine (4.6 g; 0.075 mole) in water/ethanol (50 ml/30 ml) was stirred and boiled under reflux for 3 hours. The cloudy solution was cooled in the refrigerator and the resultant yellow solid filtered off, washed with water, sucked dry and recrystallised from ethanol to give the title compound (14.5 g; 87%) m.p. 170° C.

EXAMPLE 2-23

Similarly, there were prepared:
5-Benzylidene-3-n-butylhydantoin, m.p. 151° C.

3-n-Butyl-5-(4-chlorobenzylidene) hydantoin, m.p. 264° C.

5-(2-Bromobenzylidene)-3-n-butylhydantoin, m.p. 130° C.

3-n-Butyl-5-(3,4-dimethoxybenzylidene) hydantoin, m.p. 188° C.

3-n-Butyl-5-(3-methoxy-4-pentyloxybenzylidene) hydantoin, m.p. 122° C.

3-n-Butyl-5-(4-carboxybenzylidene) hydantoin, m.p. >300° C.

3-n-Butyl-5-(4-hydroxybenzylidene) hydantoin, m.p. 234° C.

3-n-Butyl-5-(3-hydroxy-4-methoxybenzylidene) hydantoin, m.p. 185° C.

3-n-Butyl-5-(4-t-butylbenzylidene) hydantoin, m.p. 175° C.

3-n-Butyl-5-(4-cyanobenzylidene) hydantoin, m.p. 217° C.

3-n-Butyl-5-(3-trifluoromethylbenzylidene) hydantoin, m.p. 182° C.

3-n-Butyl-5-(4-methoxybenzylidene) hydantoin, m.p. 177° C.

3-n-Butyl-5-(3,4-dichlorobenzylidene) hydantoin, m.p. 231° C.

3-n-Butyl-5-(3,4-methylbenzylidene) hydantoin, m.p. 178° C.

3-n-Butyl-5-(2,4-dihydroxybenzylidene) hydantoin, m.p. 240° C.

3-n-Butyl-5-(2,4,5-triethoxybenzylidene) hydantoin, m.p. 114° C.

3-n-Butyl-5-(4-phenylbenzylidene) hydantoin, m.p. 201° C.

3-n-Butyl-5-(3-allyloxy-4-methoxybenzylidene) hydantoin, m.p. 142° C.

3-n-Butyl-5-(3-phenoxybenzylidene) hydantoin, m.p. 128° C.

3-n-Butyl-5-[3-(4-t-butylphenoxy)benzylidene] hydantoin, m.p. 168° C.

3-n-Butyl-5-[3-(3-trifluoromethylphenoxy)benzylidene] hydantoin, m.p. 132° C.

3-n-Butyl-5-[3-(4-methoxyphenoxy)benzylidene] hydantoin, m.p. 110° C.

3-n-Butyl-5-[3-(3,4-dichlorophenoxy)benzylidene] hydantoin, m.p. 146° C.

EXAMPLE 24

3-n-Butyl-5-(4-methoxycarbonylbenzylidene) hydantoin 3-n-Butyl-5-(4-carboxybenzylidene) hydantoin (5.8 g; 0.02 mole) was added gradually to a stirred mixture of thionylchloride (1.5 ml; ca 0.02 mole) in methanol (100 ml.) prepared at −10° C. The mixture was gradually warmed to 40° C. and after 1 hour was boiled under reflux for 3 hours. After cooling and storage in the refrigerator, a white solid formed and was filtered off, washed with cold methanol and dried. This solid was recrystallised from ethyl acetate to give the title compound. Yield 3.2 g; m.p. 212° C.

EXAMPLE 25

3-n-Butyl-5-[4-(1,3-dioxol-2-yl)benzylidene] hydantoin

Terephthaldialdehyde (67 g; 0.5 mole), ethanediol (31 g, 0.5 mole) and p-toluenesulphonic acid (0.5 g) in benzene (400 ml.) were boiled under reflux for 2 hours, with the removal of the water formed via a Dean and Stark separator. After cooling, the mixture was washed with dilute sodium bicarbonate solution (100 ml, 2% W/V), then saturated sodium chloride solution (2×100 ml.) and dried over magnesium sulphate. After filtration, the benzene solution was evaporated in vacuo to give a straw-coloured oil containing ca 70% of the desired aldehyde, viz: 4-(1,3-dioxol-2-yl)-benzaldehyde, which was reacted with 3-n-butylhydantoin as in Example 1.

The product from the reaction was recrystallised from ethyl acetate to give the title compound as pale yellow crystals, m.p. 185° C.

EXAMPLE 26

3-n-Butyl-5-(4-formylbenzylidene) hydantoin 3-n-Butyl-5-[4-(1,3-dioxol-2-yl)benzylidene] hydantoin (2.7g; 0.0085 mole) was dissolved in acetone (100 ml.) and stirred overnight at room temperature with p-toluene sulphonic acid (0.5 g.). The hazy solution was evaporated in vacuo and the resultant solid suspended in water (100 ml) and neutralised to pH 7 using dilute sodium bicarbonate solution. The residual solid was filtered off, washed with water and dried to give the title compound m.p. 180° C.

In the following examples, hydrogenations were carried out at atmospheric pressure for up to 48 hours or in a Parr apparatus at 60 lb/sq.in. for up to 4 hours in suitable solvents, e.g. ethanol, ethyl acetate or glacial acetic acid, in the presence of palladium on carbon as catalyst.

EXAMPLE 27

3-n-Butyl-5-(2,4,5-trimethoxybenzyl) hydantoin 3-n-Butyl-5-(2,4,5-trimethoxybenzylidene) hydantoin (10.0 g; 0.03 mole) was mixed with glacial acetic acid (150 ml.) and hydrogenated in a Parr apparatus in the presence of 5% Pd/C (2 g). After 2 hours the catalyst was filtered off, washed with warm acetic acid and the colourless filtrate evaporated in vacuo to give a white crystalline solid. Recrystallisation from ethyl acetate gave the title compound, yield 9.2 g (91%), m.p. 122° C.

EXAMPLES 28 to 45

Similarly, there were prepared:

3-n-Butyl-5-(3,4-dimethoxybenzyl) hydantoin m.p. 102° C.

3-n-Butyl-5-(3-methoxy-4-pentyloxybenzyl) hydantoin, m.p. 72° C.

3-n-Butyl-5-(4-carboxybenzyl) hydantoin, m.p. 228° C.

3-n-Butyl-5-(4-fluorobenzyl) hydantoin, m.p. 148° C.

3-n-Butyl-5-(3-trifluoromethylbenzyl) hydantoin, m.p. 108° C.

3-n-Butyl-5-(4-methoxybenzyl) hydantoin, m.p. 122° C.

3-n-Butyl-5-(3,4-dimethylbenzyl) hydantoin, m.p. 127° C.

Similarly, but using ethanol as reaction solvent:

3-n-Butyl-5-[4-(1,3-dioxol-2-yl)benzyl] hydantoin, m.p. 126° C.

3-n-Butyl-5-(4-hydroxybenzyl) hydantoin, m.p. 160° C.

3-n-Butyl-5-(3-hydroxy-4-methoxybenzyl) hydantoin, m.p. 127° C.

3-n-Butyl-5-(4-tert-butylbenzyl) hydantoin, m.p. 152° C.

Similarly prepared but using ethyl acetate as reaction solvent were:

3-n-Butyl-5-(4-phenylbenzyl) hydantoin, m.p. 161° C.

3-n-Butyl-5-(2,4,5-triethoxybenzyl) hydantoin, m.p. 88° C.

3-n-Butyl-5-(3-phenoxybenzyl) hydantoin, m.p. 90° C.

3-n-Butyl-5-[3-(4-t-butylphenoxy)benzyl] hydantoin, m.p. 70° C.

3-n-Butyl-5-[3-(3-trifluoromethylphenoxy)benzyl] hydantoin, m.p. 86° C.

3-n-Butyl-5-[3-(4-methoxyphenoxy)benzyl] hydantoin, m.p. 102° C.

Similarly prepared but using glacial acetic acid as reaction solvent was:

3-n-Butyl-5-[4-(2-hydroxyethoxymethyl)benzyl] hydantoin, m.p. 100° C.

EXAMPLE 46

5-Benzyl-3-n-butylhydantoin

DL-β-phenylalanine (8.25 g, 0.05 mole) was dissolved in water (50 ml) containing sodium hydroxide (2 g. 0.05 mole), cooled to 0° C. and n-butyl-isocyanate (8.5 ml., 0.075 mole) was added gradually maintaining the temperature at 0° C. for 2 hours. The mixture was allowed to come to room temperature and stirred for 4 hours. The mixture was filtered (solid discarded) and the filtrate washed with ether. The washed filtrate was acidified with concentrated hydrochloric acid (50 ml) and heated on a steam bath for 30 minutes. After cooling to room temperature the resultant solid was separated by filtration, water washed and dried.

Recrystallisation from carbon tetrachloride gave the required product, yield 11.0 g., m.p. 143° C.

Similarly, there were prepared:

EXAMPLE 47 TO 52

3-n-Butyl-5-(4-chlorobenzyl) hydantoin, m.p. 121° C.
5-(2-Bromobenzyl)-3-n-butyl hydantoin, m.p. 127° C.
3-n-Butyl-5-(3,4-dichlorobenzyl) hydantoin, m.p. 149° C.
5-Benzyl-3-methyl hydantoin., m.p. 150° C.
5-Benzyl-3-phenyl hydantoin, m.p. 172° C.
5-Benzyl-3-n-hexyl hydantoin, m.p. 126° C.

EXAMPLE 53

3-n-Butyl-5-(4-cyanobenzyl) hydantoin 3-n-Butyl-5-[4-(1,3-dioxol-2-yl)benzyl] hydantoin (5.5 g., 0.017 mole) was dissolved in acetone (150 ml.) and stirred overnight at room temperature with p-toluene sulphonic acid (0.5 g). The acetone was evaporated off in vacuo and the residual oily solid partitioned between water and chloroform. The chloroform phase was washed with sodium carbonate solution (2% W/V), then evaporated in vacuo to give a yellow oil which slowly crystallised and was recrystallised from petroleum ether 60°/80° C./ethyl acetate (3/1 V/V) to give 3-n-butyl-5-(4-formylbenzyl) hydantoin, 4.5 g (95%), m.p. 160° C.

The formyl compound (4.3 g., 0.01 mole), N,O-bis (trifluoroacetyl)hydroxylamine (3.6 g., 0.016 mole) and dry pyridine (2.6 ml. 0.032 mole) were mixed in benzene (75 ml) and heated under reflux for 2 hours. After cooling the benzene solution was washed with water (2×50 ml), dried over magnesium sulphate monohydrate and evaporated in vacuo to give an oil which slowly crystallised. This product was further purified by silica gel chromatography and recrystallisation from a small volume of ethyl acetate to give the title compound, yield 2.5 g., m.p. 136° C.

EXAMPLE 54

3-n-Butyl-5-(4-methoxycarbonylbenzyl) hydantoin 3-n-Butyl-5-(4-carboxybenzyl) hydantoin (7.2 g., 0.025 mole) was added to a stirred solution of thionyl chloride (1.8 ml., 0.025 mole) in methanol (100 ml) prepared at −5° to −10° C. The mixture was allowed to come to room temperature and finally heated under reflux for 1 hour. After cooling, the clear solution was evaporated in vacuo to dryness and the resultant white crystalline solid was recrystallised from ethyl acetate to give the title compound. Yield 7.1 g (94%) m.p. 144° C.

EXAMPLE 55

5-Benzyl-3-n-butyl-1-methylhydantoin

5-Benzyl-3-n-butyl hydantoin (7.38 g, 0.03 mole) was dissolved in dimethylformamide (50 ml.) and added dropwise with stirring to a suspension of sodium hydride (1.44 g. 50% oil dispersion) in dimethylformamide (20 ml). When gassing ceased, iodomethane (2 ml) was added and the mixture warmed to 50° C. and maintained at 50° C. for 5 hours. The mixture was poured into ice/water (500 ml) and extracted with ether. The ether extract was evaporated in vacuo to give a colourless oil which faild to crystallise and was distilled in a Kugelrohr apparatus to give the title compound (6.6 g; 85%) b.p. 145° C./0.02 mm.

EXAMPLE 56 TO 63

Similarly there were prepared:
5-Benzyl-3-n-butyl-1-n-hexylhydantoin, b.p. 155° C./0.02 mm (Kugelrohr)
1-Allyl-5-benzyl-3-n-butylhydantoin, b.p. 140° C./0.01 mm (Kugelrohr)
5-Benzyl-1-n-hexyl-3-methylhydantoin, m.p. 70° C.
5-Benzyl-1,3-dimethylhydantoin, m.p. 75° C.
5-Benzyl-1,3-di-n-hexylhydantoin, b.p. 200° C./0.02 mm (Kugelrohr)
5-Benzyl-1-methyl-3-phenylhydantoin, m.p. 62° C.
5-Benzyl-1-n-hexyl-3-phenylhydantoin, b.p. 210° C./0.01 mm (Kugelrohr)
1-Allyl-5-benzyl-3-phenylhydantoin, m.p. 66° C.

In the following Examples 64 to 66 the starting 3,5-dibenzylhydantoin was prepared by the method of H. Finkbeiner *Journal of Organic Chemistry* 30, 3414 (1965).

3,5-Dibenzyl-1-methylhydantoin, b.p. 195° C./0.01 mm (Kugelrohr)
3,5-Dibenzyl-1-n-hexylhydantoin, b.p. 225° C./0.01 mm (Kugelrohr)
1-Allyl-3,5-dibenzylhydantoin, b.p. 210° C./0.01 mm (Kugelrohr)

EXAMPLE 67

3-n-Butyl-5-(thiophen-2-yl methylene) hydantoin

A mixture of thiophene-2-carboxaldehyde (5.6 g; 0.05 mole), 3-n-butylhydantoin (7.8 g; 0.05 mole) and ethanolamine (4.6 g; 0.075 mole) in water/ethanol (50 ml/30 ml) was stirred and boiled under reflux for 4 hours. The mixture was cooled in the refrigerator and the resultant brownish yellow crystals filtered off, washed with water, sucked dry and recrystallised from ethyl acetate (with carbon treatment) to give the title compound (6.4 g; 51%) having m.p. 140° C.

EXAMPLE 68 TO 70

Similarly, there were prepared:
3-n-Butyl-5-(5-methylthiophen-2-yl methylene) hydantoin, m.p. 146° C.
3-n-Butyl-5-(3-methylthiophen-2-yl methylene) hydantoin, m.p. 124° C.
3-n-Butyl-5-(5-phenylthiophen-2-yl methylene) hydantoin, m.p. 220° C.

In the following Examples the required thiophene amino acids were prepared from the appropriate aldehydes by the methods of P. L. Julian and B. M. Sturgis, *Journal of the Americal Chemical Society* 57, 1126 (1935) and B. F. Crowe and F. F. Nord, *Journal of Organic Chemistry* 15, 689, (1950).

EXAMPLE 71

3-n-Butyl-5-(5-Methylthiophen-2-yl methyl) hydantoin

DL-β-(5-Methylthiophen-2-yl)alanine (4.1 g; 0.022 mole) was dissolved in 2 N sodium hydroxide solution (11 ml; 0.022 mole), cooled to 0° C. and n-butyl-isocyanate (3.75 ml; 0.033 mole) added gradually maintaining the temperature at 0° C. for 2 hours. The mixture was allowed to come to room temperature and stirred overnight. The mixture was filtered (solid discarded) and the filtrate washed with ether. The washed filtrate was acidified with concentrated hydrochloric acid (11 ml) and heated on a steam bath for 1 hour. After cooling to room temperature the resultant solid was separated by filtration, water washed and dried. Recrystallisation from ethyl acetate gave the title compound. Yield 4.2 g (72%), m.p. 107° C.

Similarly there were prepared:
3-n-Butyl-5-(thiophen-2-yl methyl) hydantoin, m.p. 150° C.
3-n-Butyl-5-(3-methylthiophen-2-yl methyl) hydantoin, m.p. 94° C.
3-n-Butyl-5-(5-phenylthiophen-2-yl methyl) hydantoin, m.p. 127° C.

The following Examples 72–78 illustrate pharmaceutical formulations containing as active compound 3-n-butyl-5-(thiophen-2-yl-methyl)hydantoin or 3-n-butyl-5-(2,4,5-triethoxybenzyl)hydantoin.

EXAMPLE 72

Soft gelatin capsules were prepared using the following ingredients:

|  | Quantity (mg/capsule) |
|---|---|
| Active compound | 20 |
| Propyl gallate | 0.03 |
| Fractionated Coconut Oil B.P.C. | 70 |

The above ingredients were mixed and filled into soft gelatin capsules, the main shell components of which were gelatin and glycerine.

EXAMPLE 73

Hard gelatin capsules were prepared using the following ingredients:

|  | Quantity(mg/capsule) |
|---|---|
| Active compound | 25 |
| Silicon dioxide (fumed) | 25 |
| Lactose | 50 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 74

An ointment was made up from the following ingredients:

| Active compound | 2% by weight |
|---|---|
| Butylated hydroxyanisole B.P. | 0.04% by weight |
| White soft paraffin | q.s. 100% |

The hydroxyanisole was dissolved in the melted paraffin and the active compound then added in, and the mixture allowed to cool.

EXAMPLE 75

A topical cream containing 1% of the compound was prepared as follows:

|  | grams: |
|---|---|
| Active compound | 1 |
| Cetomacrogol 1000 | 3 |
| Cetostearyl alcohol | 10 |
| Liquid Paraffin | 7 |
| Butylated hydroxyanisole B.P. | 0.04 |
| Distilled Water | to 100.0 |

The active compound was mixed with the hydroxyanisole and suspended in the liquid paraffin. The cetostearyl alcohol was added and the mixture heated to 70° C. with stirring. The cetomacrogol 1000 was then dissolved in 60 g. of water heated to 70° C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 76

Suppositories containing 30 and 60 mg. of the compound were prepared as follows:

| Active compound | 3 g |
|---|---|
| Henkel base | 97 g |

The active compound was mixed with the Henkel base which had been previously melted using the minimum amount of heat possible. The mixture was then poured into suppository moulds of a nominal capacity of 1 g. or 2 g. as desired, to produce suppositories each containing 25 mg. or 50 mg. of the active compound.

EXAMPLE 77

An aerosol was prepared containing the following ingredients:

| | Quantity per ml. | |
|---|---|---|
| Active compound | 10.00 | mg. |
| Propylene glycol | 10.00 | mg. |
| Dichlorotetrafluoroethane (Propellant 114) | 500 | mg. |
| Dichlorodifluoromethane (Propellant 12) | 900 | mg. |

The active compound was mixed with the propylene glycol and the mix added to the propellant 114, the mixture cooled to −15° to −20° C. and transferred to a filling device. At the same time a mixture of propellants 114 and 12, previously cooled to −15° to −20° C. was fed into a second filling device. A metered amount of propellant from the second filling device was introduced into a stainless steel container, followed by the required amount of material from the first filling device. The valve units were then fitted and sealed to the container. These valve units were equipped with metering device so that approximately 0.15 mg. of the active compound is released by a single actuation of the valve.

EXAMPLE 78

Tablets were prepared using the following components:

| Active compound | 15.00 | mg. |
|---|---|---|
| Microcrystalline Cellulose | 240.00 | mg. |
| Sodium Carboxymethyl Starch | 20.00 | mg. |
| Magnesium Stearate | 2.5 | mg. |
| Butylated Hydroxyanisole B.P. | 0.002 | mg. |

The hydroxyanisole was dissolved in the active compound, the solution adsorbed onto the microcrystalline cellulose. This was mixed with the sodium carboxymethyl starch and the magnesium stearate then mixed in. Finally, the mixture was compressed to form tablets.

We claim:

1. A method of treating a mammal, including a human, for an immediate hypersensitivity condition by administering an effective amount of a compound of the formula

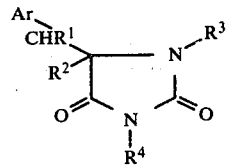

wherein
Ar is phenyl optionally substituted by up to three radicals selected from the group comprising $C_1$–$C_6$ alkoxy, halogen, 1,3-dioxol-2-yl, hydroxy $C_1$–$C_4$ alkoxy $C_1$–$C_4$ alkyl, phenyl, hydroxyl, nitrile, $C_1$–$C_4$ haloalkyl, $C_1$–$C_4$ alkyl, $C_2$–$C_4$ alkenyloxy, $C_1$–$C_4$ alkoxycarbonyl or phenoxy optionally substituted by $C_1$–$C_4$ haloalkyl, $C_1$–$C_4$ alkoxy or halogen;
or is thiophene optionally substituted by phenyl or by one or two $C_1$–$C_4$ alkyl groups;
$R^1$ and $R^2$ are independently hydrogen or taken together represent a chemical bond;
$R^3$ is hydrogen, $C_1$–$C_6$ alkyl or $C_2$–$C_4$ alkenyl; and
$R^4$ is $C_1$–$C_6$ alkyl, $C_2$–$C_4$ alkenyl, phenyl or benzyl.

2. A method according to claim 1 in which 3-n-butyl-5-(thiophen-2-yl(methyl))hydantoin is administered.

3. A method according to claim 1 in which 3-n-butyl-5-(2,4,5-trimethoxybenzyl)hydantoin is administered.

* * * * *